United States Patent
Yoshikawa

(10) Patent No.: US 9,280,817 B2
(45) Date of Patent: Mar. 8, 2016

(54) IMAGE DIAGNOSTIC DEVICE AND AN IMAGE DIAGNOSTIC METHOD FOR AUTOMATIC ASSESSMENT OF THE START AND END OF THE INFLOW OF A CONTRAST MEDIUM

(75) Inventor: Hideki Yoshikawa, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 84 days.

(21) Appl. No.: 14/342,087

(22) PCT Filed: Jun. 26, 2012

(86) PCT No.: PCT/JP2012/066251
§ 371 (c)(1),
(2), (4) Date: Feb. 28, 2014

(87) PCT Pub. No.: WO2013/057982
PCT Pub. Date: Apr. 25, 2013

(65) Prior Publication Data
US 2014/0219539 A1    Aug. 7, 2014

(30) Foreign Application Priority Data
Oct. 19, 2011   (JP) .................. 2011-229323

(51) Int. Cl.
| A61B 8/06 | (2006.01) |
| G06T 7/00 | (2006.01) |
| A61B 5/055 | (2006.01) |
| A61B 6/00 | (2006.01) |
| A61B 8/08 | (2006.01) |
| G01R 33/56 | (2006.01) |
| A61B 5/00 | (2006.01) |
| G01R 33/563 | (2006.01) |

(52) U.S. Cl.
CPC .............. *G06T 7/0012* (2013.01); *A61B 5/055* (2013.01); *A61B 5/489* (2013.01); *A61B 6/481* (2013.01); *A61B 6/504* (2013.01); *A61B 8/06* (2013.01); *A61B 8/481* (2013.01); *G01R 33/5601* (2013.01); *G06T 7/0016* (2013.01); *G01R 33/5635* (2013.01); *G06T 2207/10016* (2013.01); *G06T 2207/10081* (2013.01); *G06T 2207/10088* (2013.01); *G06T 2207/10132* (2013.01); *G06T 2207/30104* (2013.01)

(58) Field of Classification Search
None
See application file for complete search history.

(56) References Cited

U.S. PATENT DOCUMENTS

2011/0075904 A1 *  3/2011  Yoshikawa et al. ........... 382/131

FOREIGN PATENT DOCUMENTS

| JP | 64-86942 A | 3/1989 |
| JP | 2005-307961 A | 11/2005 |
| JP | 2006-102030 A | 4/2006 |
| JP | 2006-527041 A | 11/2006 |

(Continued)

OTHER PUBLICATIONS

International Search Report from International Application No. PCT/JP12/066251 mailed Aug. 7, 2012.

(Continued)

*Primary Examiner* — Siamak Harandi
(74) *Attorney, Agent, or Firm* — Brundidge & Stanger, P.C.

(57) ABSTRACT

Provided is an image diagnostic device with which the start and end of the in-flow of a contrast medium are automatically assessed. An image diagnostic device assesses the start and end times of the in-flow of a contrast medium into organs in a lifeform which is a subject.

13 Claims, 14 Drawing Sheets

(56) References Cited

FOREIGN PATENT DOCUMENTS

| JP | 2010-512900 A | 4/2010 |
| JP | 2011-110211 A | 6/2011 |
| JP | 2011-172819 A | 9/2011 |
| WO | 2004/110279 A1 | 12/2004 |
| WO | 2009/110308 A1 | 9/2009 |

OTHER PUBLICATIONS

Beers B. E. V et al., : "Hepatic Perfusion Parameters in Chronic Liver Disease" Dynamic CT Measurements Correlated with Disease Severity, AJR 176, pp. 667-673, Mar. 2001.

* cited by examiner

FIG. 12
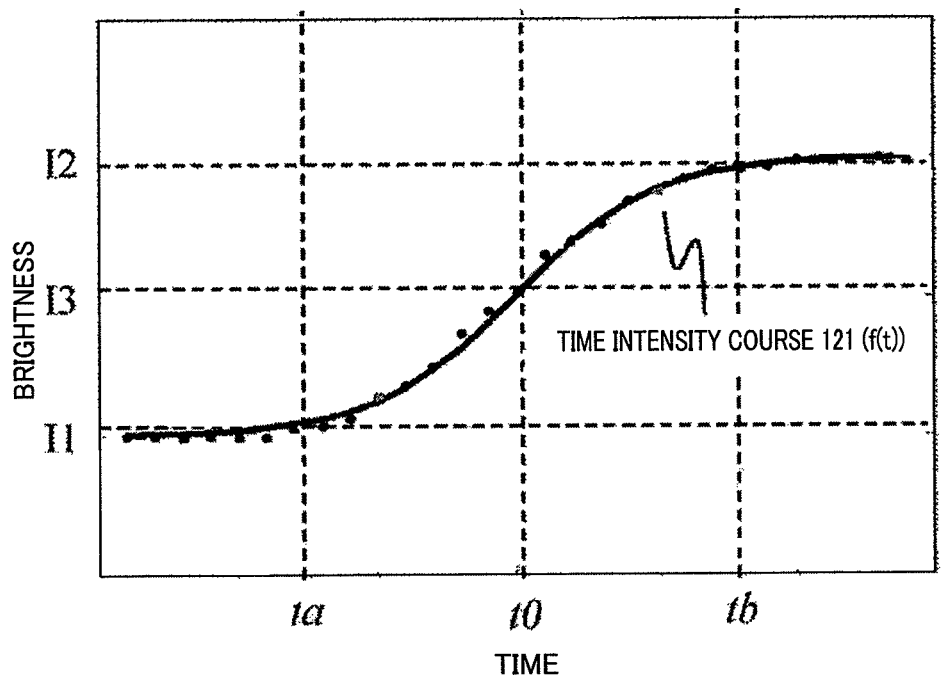
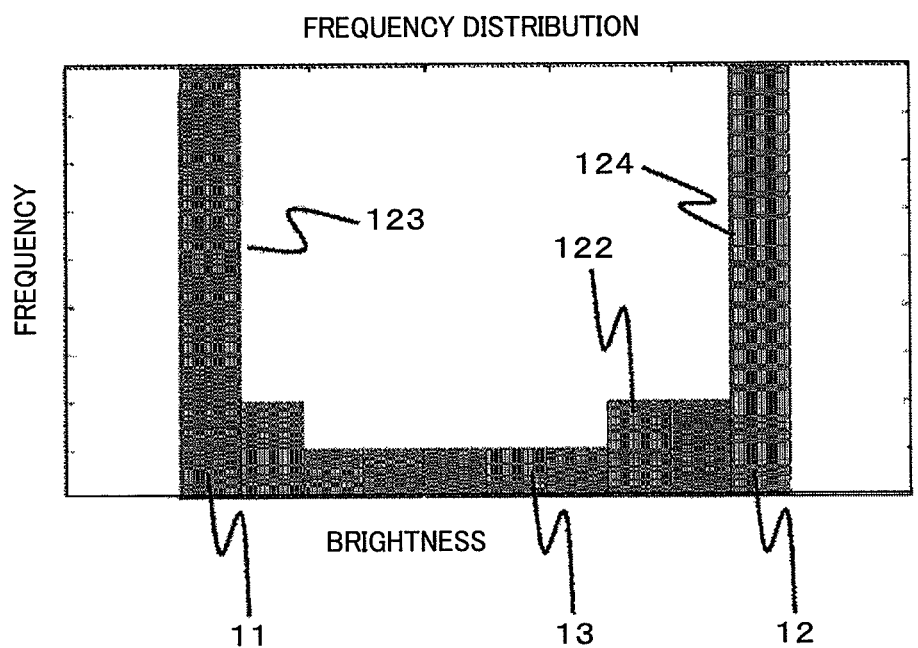

IMAGE DIAGNOSTIC DEVICE AND AN IMAGE DIAGNOSTIC METHOD FOR AUTOMATIC ASSESSMENT OF THE START AND END OF THE INFLOW OF A CONTRAST MEDIUM

CROSS REFERENCED TO RELATED APPLICATION

The present application is a U.S. National Stage filing under 35 U.S.C. §371 from PCT/JP2012/066251, filed Jun. 26, 2012 and claims foreign priority from Japanese Application No. 2011-229323, filed Oct. 19, 2011, the contents of which are incorporated herein by reference.

TECHNICAL FIELD

The present invention relates to a contrast diagnosis to evaluate vessel distribution and a bloodstream dynamic state by administering a contrast medium into a living body, and particularly to a dynamic state evaluation technique to automatically assess and display the start and end of contrast.

BACKGROUND ART

Image diagnostic devices used in medical practice such as an ultrasonic device, a CT (Computed Tomography) device, and an MRI (Magnetic Resonance Imaging) device have been widely spread as means to image tissue in a living body. A dedicated contrast medium has been developed for each diagnostic device, and information related to the dynamic state of a bloodstream that cannot be generally imaged can be obtained by using the contrast medium.

A liver tumor is one of lesions for which observation of the bloodstream dynamic state is especially effective. Regarding the liver tumor, a known fact is that portal vessels governing the lesion part are transited to artery vessels in the course in which the liver tumor is deteriorated from a precancer state such as hepatitis or cirrhosis to liver cancer. In the case of the liver tumor at an early stage, a known fact is that portal vessels in which blood having flowed through a digestive system flows are dominant. However, as the disease progresses, artery vessels become dominant (Non-patent document 1).

The artery vessels are different from the portal vessels in the start time of contrast or the inflow rate of the contrast medium due to a difference between circulation routes. Therefore, an early stage of contrast and the next stage thereof are expressed as an artery phase and a portal phase, respectively, in a contrast inspection in some cases. A time intensity course obtained by plotting time changes of brightness along with inflow of the contrast medium is useful in evaluating such a difference of the bloodstream dynamic state. Using a contrast image of the lesion part or the time intensity course, the lesion can be promptly detected and the activation level can be determined. Further, the contract inspection is considered to be important as an effective imaging technique in a differential diagnosis for a lesion because the bloodstream dynamic state is changed depending on the type of lesion such as hepatocellular cancer, metastatic cancer, or a cyst.

In addition, the evaluation of the bloodstream dynamic state is effective in determining the effect of cancer treatment. In the case of RF treatment or medical therapy using medicine, the bloodstream dynamic state is an important target for observation other than the size of a tumor. This is because even if the size of a tumor is not changed on an image, the effectiveness of the treatment can be determined on the basis of disappearance of tumor vessels or a decrease in blood flow. Especially, in the case of a treatment method targeting vessels serving as nutrient supply routes to a tumor such as an angiogenesis inhibitor or vascular embolization therapy, not only the presence or absence of a bloodstream to the lesion, but also the bloodstream dynamic state becomes an important target for observation in the determination of the effect because in the case where the bloodstream can be observed, the following treatment policy is changed depending on whether the bloodstream is of artery or portal.

As described above, when the bloodstream dynamic state is evaluated to obtain information useful in a differential diagnosis or in the determination of the treatment effect, it is important to discriminate the artery phase from the portal phase using a series of contrast processes such as the start of inflow of the contrast medium into the artery vessels or the portal vessels. Patent documents 1 and 2 are relevant prior arts. The content described in Patent document 1 relates to a technique of evaluating the angiogenesis of a tumor, and is a method of modeling measurement values with a model curve. The content described in Patent document 2 relates to a system that calculates the average speed of a bloodstream by associating a function having S-shaped characteristics with a time function representing a contrast process. According to the content described in Patent document 2, the reflux of a contrast medium to tissue again is associated with an S-shaped function, and the average speed or average flow rate of a bloodstream at the time of reflux is estimated.

PRIOR ART DOCUMENT

Patent Document

Patent document 1: WO2008/053268
Patent document 2: WO2004/110279

Non-Patent Document

Non-patent document 1: Beers B. E. V et al.: AJR 176, 667. 2001.

SUMMARY OF THE INVENTION

Technical Problem

In the methods described in Patent document 1 and Patent document 2, a time intensity course is modeled, and a bloodstream dynamic state is evaluated using a characteristic value such as the maximum value. Therefore, although much information related to the bloodstream can be obtained using the characteristic value of the model function, the methods are not necessarily suitable for discrimination of the artery phase and the portal phase using the contract course. Each duration of the artery phase and the portal phase is about two seconds, and corresponds to a main inclination part of the time intensity course. For example, in the case where the duration of the entire time intensity course is wider than that of the artery phase or the portal phase, there is a possibility that an error at the inclination part of interest becomes large because the model function is adjusted in a range except the inclination part. Thus, in order to eliminate the error, a process of limiting the evaluation range or an addition process of increasing parameters of the model function is needed, and the number of processing steps is increased.

An object of the present invention is to provide an image diagnostic device and an image assessment method that can automatically assess the start and end of inflow of a contrast medium on the basis of a measured time intensity course.

Solution to Problem

In order to achieve the above-described object, the present invention provides an image diagnostic device that evaluates the bloodstream dynamic state of a subject, the device including: an image acquisition unit that acquires an image on the basis of a signal received from the subject; an assessment unit that assesses the start and end of inflow of a contrast medium on the basis of the shape of a time intensity course representing time changes of the brightness of the image; and a display unit that displays a result assessed by the assessment unit.

Further, in order to achieve the above-described object, the present invention provides an image assessment method that assesses the start time and the end time of inflow of a contrast medium on the basis of the shape of a time intensity course representing time changes of the brightness of an image based on a signal received from a subject.

Advantageous Effect of the Invention

According to the present invention, it is possible to realize an image diagnostic device and an image assessment method provided with a function of automatically assessing the start and end times of inflow of a contrast medium fast with a high degree of accuracy.

BRIEF DESCRIPTION OF THE DRAWINGS

FIG. 12 is a diagram for showing use of frequency distribution in the device of the first example.

BEST MODE FOR CARRYING OUT THE INVENTION

Hereinafter, various examples of the present invention will be described using the drawings.

FIRST EXAMPLE

A first example relates to an image diagnostic device that evaluates the bloodstream dynamic state of tissue in a living body that is a subject, and particularly to an image diagnostic device that evaluates the bloodstream dynamic state of the subject and includes an image acquisition unit that acquires an image on the basis of a signal received from the subject, an assessment unit that assesses the start and end of inflow of a contrast medium on the basis of the shape of a time intensity course representing time changes of the brightness of the image, and a display unit that displays a result assessed by the assessment unit. Further, the example is an example of an image assessment method in which the start time and the end time of inflow of a contrast medium are assessed on the basis of the shape of a time intensity course representing time changes of the brightness of an image based on a signal received from a subject. Further, the example relates to an image diagnostic method in an image diagnostic device that includes a processing unit and a display unit to evaluate the bloodstream dynamic state of a subject. The example is an example of an image assessment method in which the processing unit creates a time intensity course representing time changes of the brightness of an image that is acquired by an image acquisition unit and that is based on a signal received from a subject, and assesses the start time and the end time of inflow of a contrast medium on the basis of the shape of the created time intensity course, and the time intensity course, the start time and the end time of the inflow of the contrast medium, and image information from the image acquisition unit at the start time and the end time of the inflow can be displayed on the display unit. It should be noted that information input from the image acquisition unit into the image diagnostic device can contain not only bloodstream information, but also image information and image data of tissue in a living body acquired by the image acquisition unit.

Figure 1:
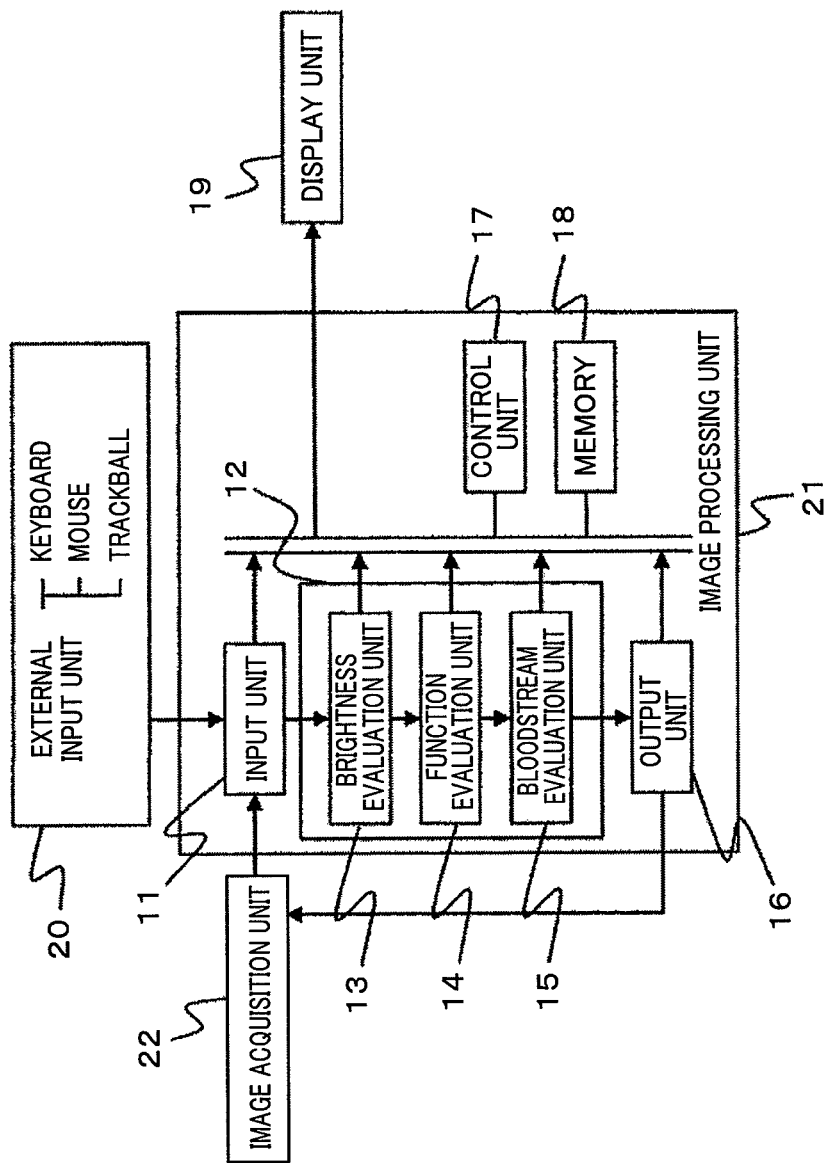
FIG. 1 is a block diagram for showing a configuration example of an image diagnostic device according to a first example.

FIG. 1 shows a block diagram of an image diagnostic device of the first example. The image diagnostic device of the first example is configured using an image acquisition unit 22, an image processing unit 21, an external input unit 20 used to operate the image processing unit 21 by an operator, and a display unit 19 for displaying output information of the image processing unit 21. The image processing unit 21 includes an input unit 11 that inputs bloodstream information acquired by the image acquisition unit 22, an assessment unit 12 that assesses the start and end of inflow of a contrast medium to a subject from an image including the input bloodstream information, an output unit 16 that outputs from the image processing unit 21 to the outside, a control unit 17 that controls all processes performed inside the image processing unit 21, and a memory 18 that temporarily holds information input to the input unit 11 and information calculated inside the image processing unit 21.

The assessment unit 12 includes a brightness evaluation unit 13 that calculates a time intensity course representing time changes of brightness using the bloodstream information input from the input unit 11, a function evaluation unit 14 that approximates the time intensity course with an S-shaped function to create a model function, and a bloodstream evaluation unit 15 that evaluates a bloodstream dynamic state and the like using the model function.

The image acquisition unit 22 indicates a general device such as the ultrasonograph, an MRI device, or a CT device that can acquire a signal from a medical agent (including a contrast medium) administered into the blood. The image diagnostic device of the example can be realized using a normal computer device. Specifically, the computer device is configured using a CPU (Central Processing Unit) that is a processing unit, a memory that is a storage unit, and input and output interfaces that are input and output units.

Of the functional blocks of the image processing unit 21 in FIG. 1, the input unit 11 and the output unit 16 correspond to the input and output interfaces, respectively; the memory 18 corresponds to the memory; and the control unit 17 corresponds to the CPU. Further, the brightness evaluation unit 13, the function evaluation unit 14, and the bloodstream evaluation unit 15 that are functional blocks configuring the assessment unit 12 are stored in the memory and correspond to functional programs executed by the CPU. Further, the display unit 19 and the external input unit 20 correspond to a display and a keyboard that come with the computer device, respectively. In the description, the assessment unit 12 configured using the brightness evaluation unit 13, the function evaluation unit 14, and the bloodstream evaluation unit 15, and the control unit 17 are collectively referred to as a processing unit in some cases.

Figure 2:
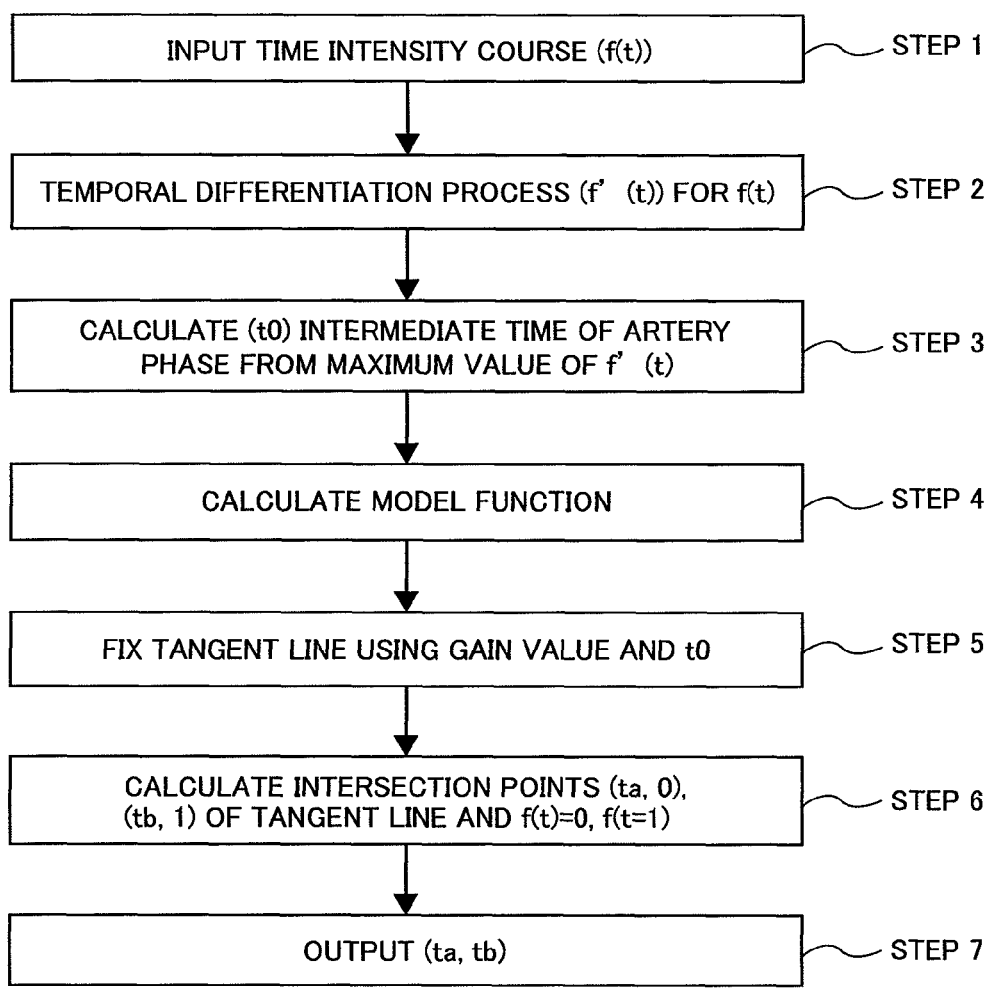
FIG. 2 is a diagram for explaining processing steps of the device of the first example.

Next, an evaluation method of a bloodstream by the image diagnostic device of the example will be described using a flowchart shown in FIG. 2 and various graphs shown in FIG. 3. The dimension of information input from the image acquisition unit 22 to the input unit 11 is not particularly limited. However, as an example, the example assumes a case in which the artery phase of bloodstream is assessed using information to be handled as image information. The operations of the flowchart of FIG. 2 are mainly performed by the image processing unit 21 of FIG. 1, especially, the input unit 11, the assessment unit 12 configured using the brightness evaluation unit 13, the function evaluation unit 14, and the bloodstream evaluation unit 15, and the output unit 16. More specifically, the operations of the flowchart are programs executed by the CPU except input and output steps.

First, time-series image data acquired by the image acquisition unit 22 is input to the input unit 11 in FIG. 2 (Step 1). As an input method, while accessing the image acquisition unit 22 in a wired or wireless manner, desired image data is selected from stored data therein. Further, the data may be input using a medium such as a flash memory, and the input means is not limited. The image data input to the input unit 11 is output to the brightness evaluation unit 13 of the assessment unit 12. The brightness evaluation unit 13 designates ranges of space and time used to evaluate the bloodstream for the received image data. Next, a space average process is performed for the image data within the designated ranges to convert the image data into a one-dimensional time intensity course (f(t)) representing time changes of brightness. Next, a temporal differentiation process for performing temporal differentiation (f'(t)) is performed for f(t) (Step 2).

Figure 3:
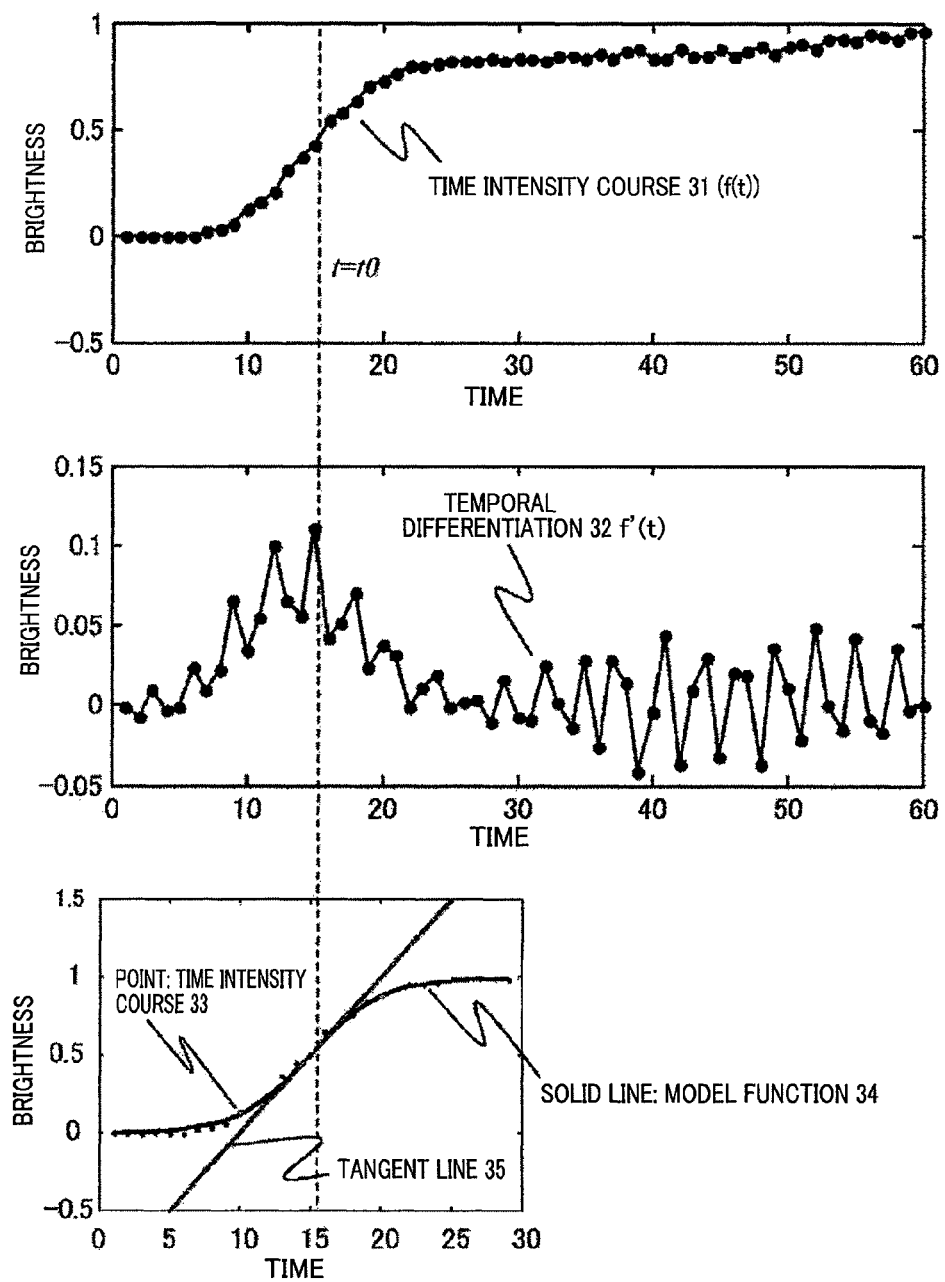
FIG. 3 is a diagram for showing a step of calculating a model function from a time intensity course of the device of the first example.

FIG. 3 shows the above-described time intensity course and results of the temporal differentiation process. Temporal differentiation 32 represents time changes of a time intensity course 31. Specifically, the maximum value of the temporal differentiation 32 f'(t) indicates a point of the steepest inclination where the value of the time intensity course 31 f(t) increases, and the time (t0) when the maximum value was obtained corresponds to substantially the center of the artery phase. In FIG. 3, the reference numeral 33 denotes a time intensity course around t0 of the time intensity course 31, 34 denotes a model function, and 35 denotes a tangent line.

Next, the model function on the basis of the S-shaped function is calculated by an approximate process (Step 4). The S-shaped function includes a sigmoid function, the Gompertz function, a cumulative normal distribution function, or the like. The type of S-shaped function is not limited in the example. However, the example will be described using an example of the sigmoid function shown in the following Equation (1). The S-shaped function such as the sigmoid function is preliminarily stored in the memory 18. However, the operator can add the same from the input unit 11 using the external input unit 20 if needed.

$$f_s(t) = \frac{a}{\{1 + \exp(-\alpha t)\}} + b \quad \text{[Equation 1]}$$

wherein α is referred to as a gain value representing the inclination of the sigmoid function. The advantages using the sigmoid function will be described later.

In Step 4 that follows, the time intensity course (f(t)) is modeled using the sigmoid function. However, there are three variables in the state of Equation (1), and a parallel shift along the t-axis is further needed. Thus, in order to simplify the process, the minimum value (min(f(t))) is first subtracted from the time intensity course (f(t)), and the resultant is divided by the maximum value (max[(f(t)−min(f(t)))]). Accordingly, the range of f(t) can be limited to (0, 1), and at the same time, the variable used to perform the modeling can be limited to the gain value. Further, Equation (2) obtained by moving in the temporal axis direction by t0 is defined, so that the inflection point of the sigmoid function is allowed to be moved to substantially the center position of the artery phase.

$$f_s(t) = \frac{1}{\{1 + \exp[-\alpha(t - t0)]\}} \quad \text{[Equation 2]}$$

The gain value is specified using a well-known fitting method. In the case of using, for example, a least-square method, RMS (Root Mean Square) defined in Equation (3) is calculated using various gain values α, and the model function ($f_m(t)$) is created using the gain value α that minimizes the RMS.

$$RMS = \sqrt{\frac{1}{T}\sum_{t=1}^{t=T}(f(t) - f_s(t))} \quad \text{[Equation 3]}$$

wherein T represents a duration in which the fitting process is performed. In order to perform the fitting process with a high degree of accuracy at the inclination part of the S-shaped function, the range of the time intensity course (f(t)) is desirably limited from t=0 to t=2×t0.

It should be noted that the above-described process of simplifying the fitting process can be freely selected by the operator. In the case where the process of simplifying the fitting process is not performed, the fitting process can be performed on the assumption that all variables of the S-shaped function are those for the fitting process.

Next, the tangent line at t=t0 is calculated using the model function ($f_m(t)$) (Step 5), and further, times t=ta and t=tb when the values of the tangent line become 0 and 1, respectively, are calculated (Step 6).

The sigmoid function described in Equation (2) has the nature of the following equation.

$$f(t0)=1/2, f'(t0)=\alpha/4, f''(t0)=0 \quad \text{[Equation 4]}$$

Thus, the tangent line g(t) at the inflection point located at substantially the center of the artery phase, and the ta and tb are described in the following simple formats.

$$\begin{cases} g(t) = \frac{\alpha}{4}t + \frac{1}{2} \\ ta = g(0) = -\frac{2}{\alpha} \\ tb = g(1) = \frac{2}{\alpha} \end{cases} \quad \text{[Equation 5]}$$

Specifically, when the gain α of the model function is fixed, the ta and tb are fixed with a simple calculation. The ta and tb mean the start and end times of the inflow of the contrast medium into an artery area. One of the advantages using the sigmoid function is easiness of the calculation. The fixed ta and tb are output to and stored into the memory 18 (Step 7). It should be noted that the tangent line g(0) and the tangent line g(1) in the above equation are asymptotic lines provided above and under the model function. In other words, the assessment of the times ta and tb as the start and end times of the inflow of the contrast medium is performed on the basis of the intersection points of the tangent line at the inflection point t0 of the model function and the asymptotic lines provided above and under the model function. The result of the fitting in Step 4 is displayed on the display unit 19 through the output unit 16.

Figure 4:
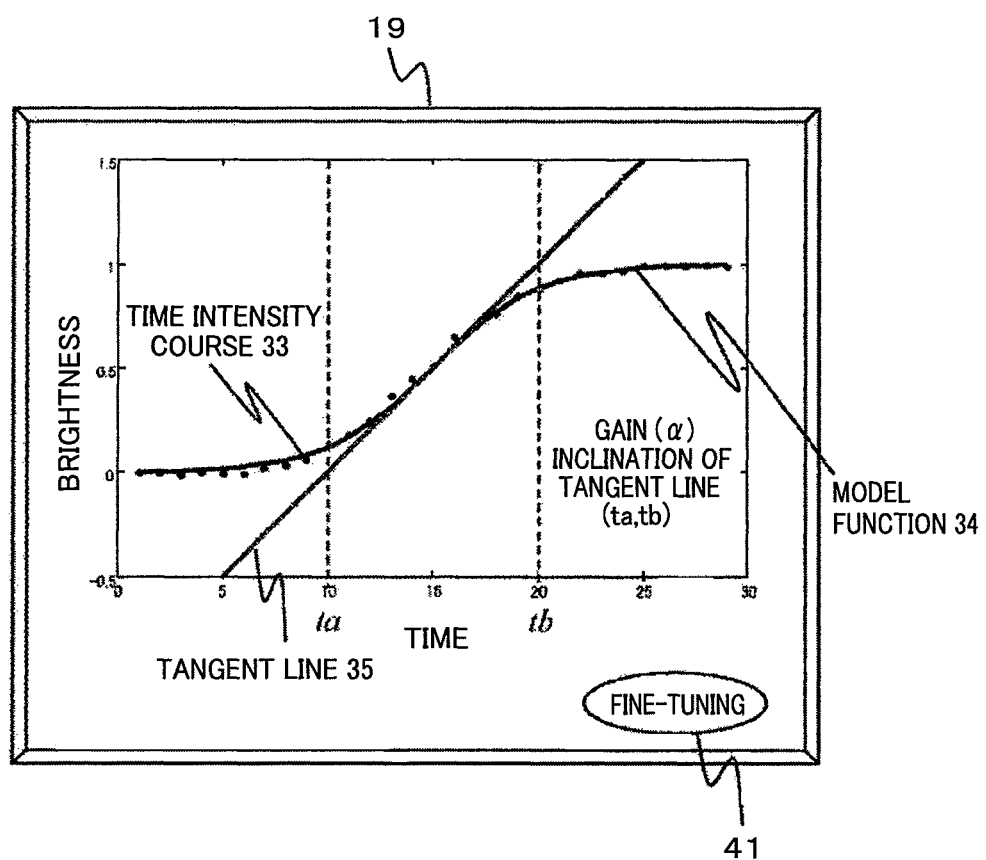
FIG. 4 is a diagram for showing a first example of a display of the device of the first example.

FIG. 4 shows an example of a display configuration of the image diagnostic device in the example. On the display unit 19, the results of the processes from Step 1 to Step 4 such as the time intensity course 33, the model function 34, and the tangent line 35 can be displayed while being overlapped with each other, and can be confirmed by the operator. Further, as shown in the drawing, the gain value a and the inclination (ta, tb) of the tangent line are displayed using numbers on the display unit 19.

The main body 21 of the image diagnostic device of the example can be provided with a mechanism of fine-tuning the fitting through an external input by the operator. When a fine-tuning button 41 displayed on the display unit 19 shown in FIG. 4 is selected using the external input unit 20 such as a mouse, an arrow, a marker or the like for fine-tuning is displayed on the display unit 19.

Figure 5:
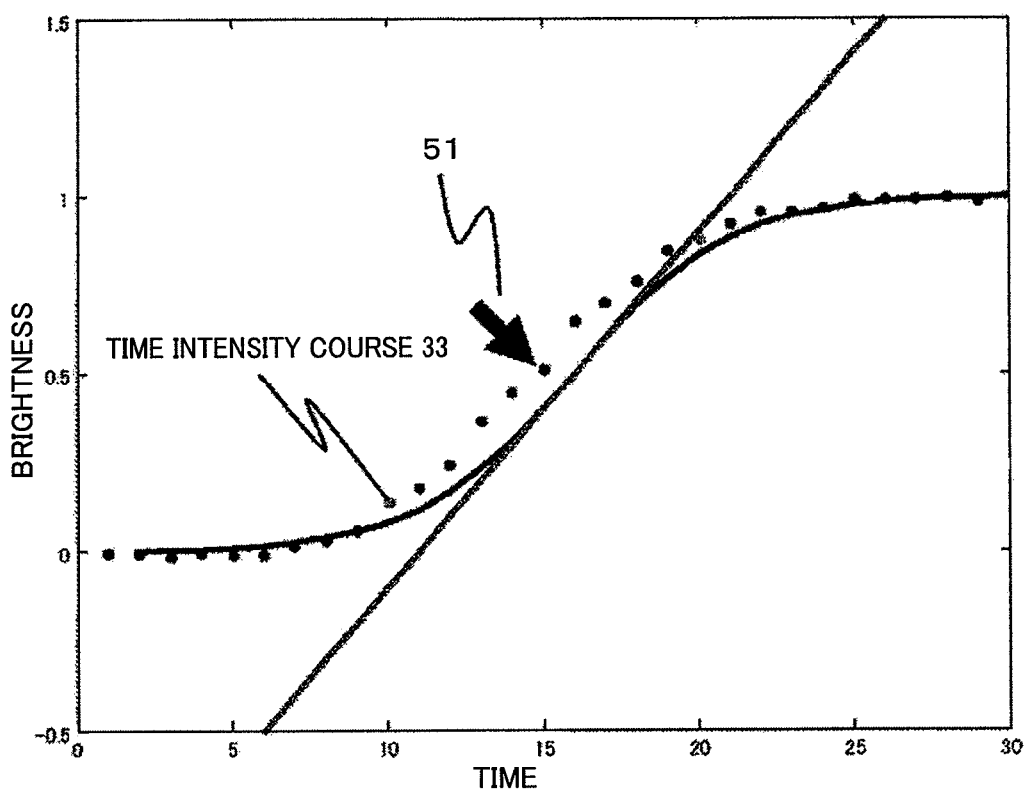
FIG. 5 is a first diagram for showing fine-tuning of the model function of the device of the first example.

As shown in FIG. 5, the parallel shift is carried out in such a manner that the operator moves an arrow 51 displayed on the screen using the external input unit 20 and selects the position of the inflection point of the model function from points of the time intensity course 33. Specifically, the time near the inflection point of the time intensity course can be input at the time of the approximate process using the external input unit 20.

Figure 6:
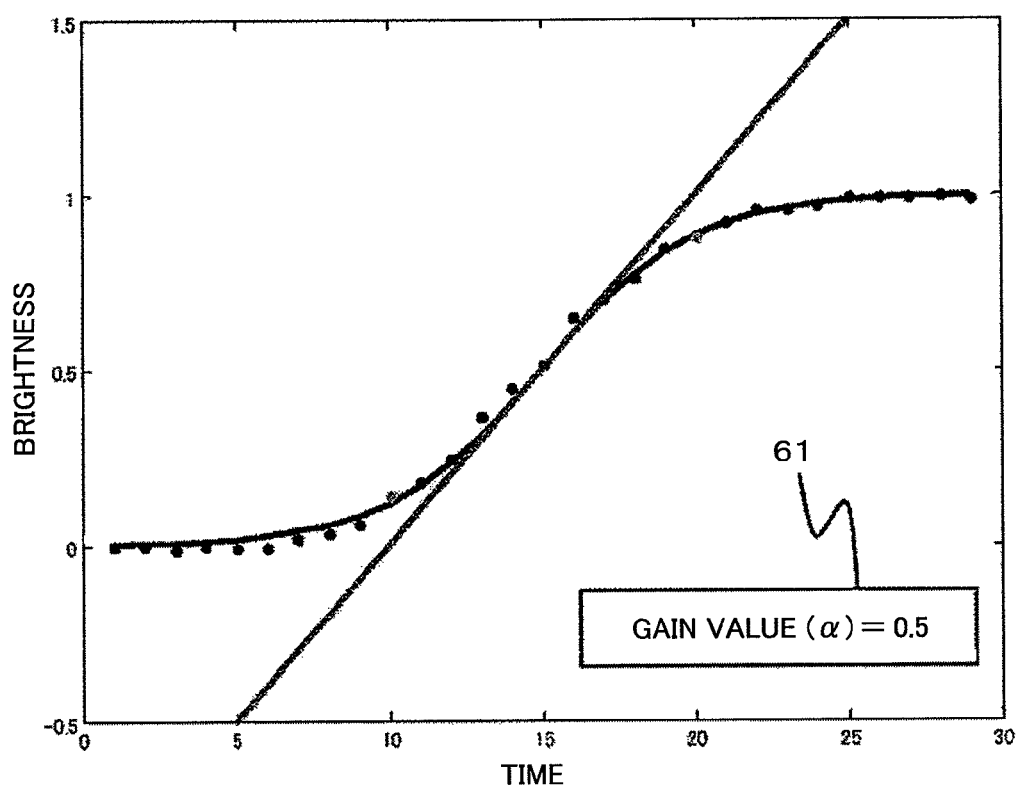
FIG. 6 is a second diagram for showing fine-tuning of the model function of the device of the first example.
Figure 7:
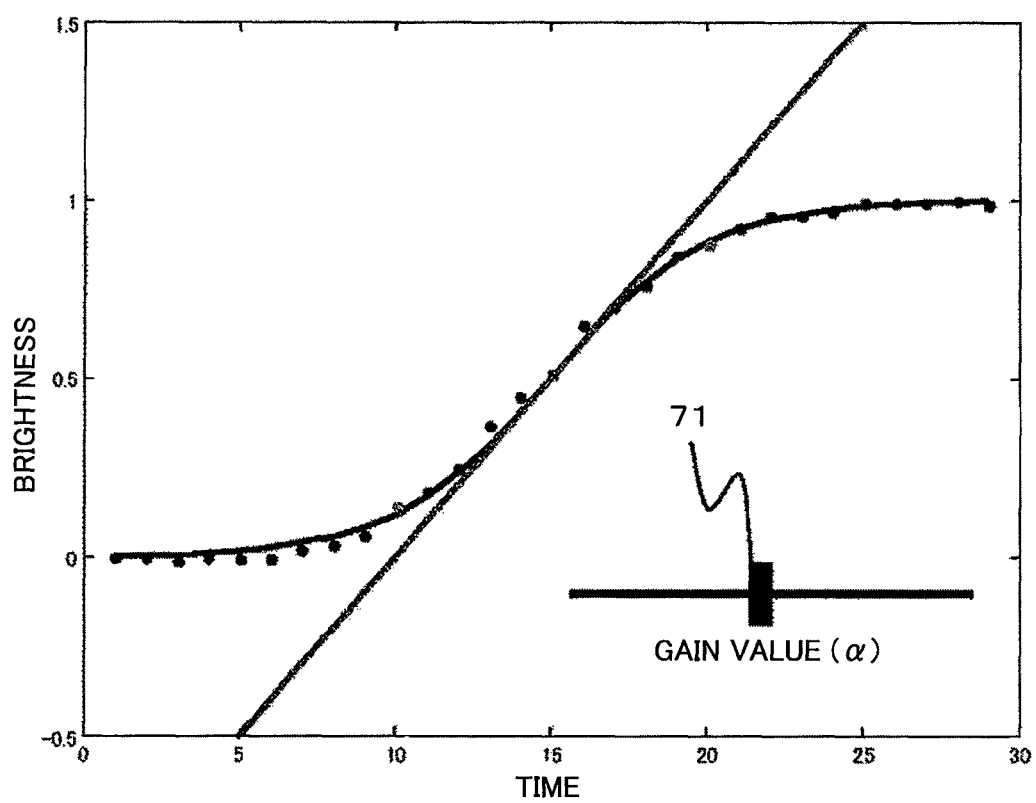
FIG. 7 is a third diagram for showing fine-tuning of the model function of the device of the first example.
Figure 8:
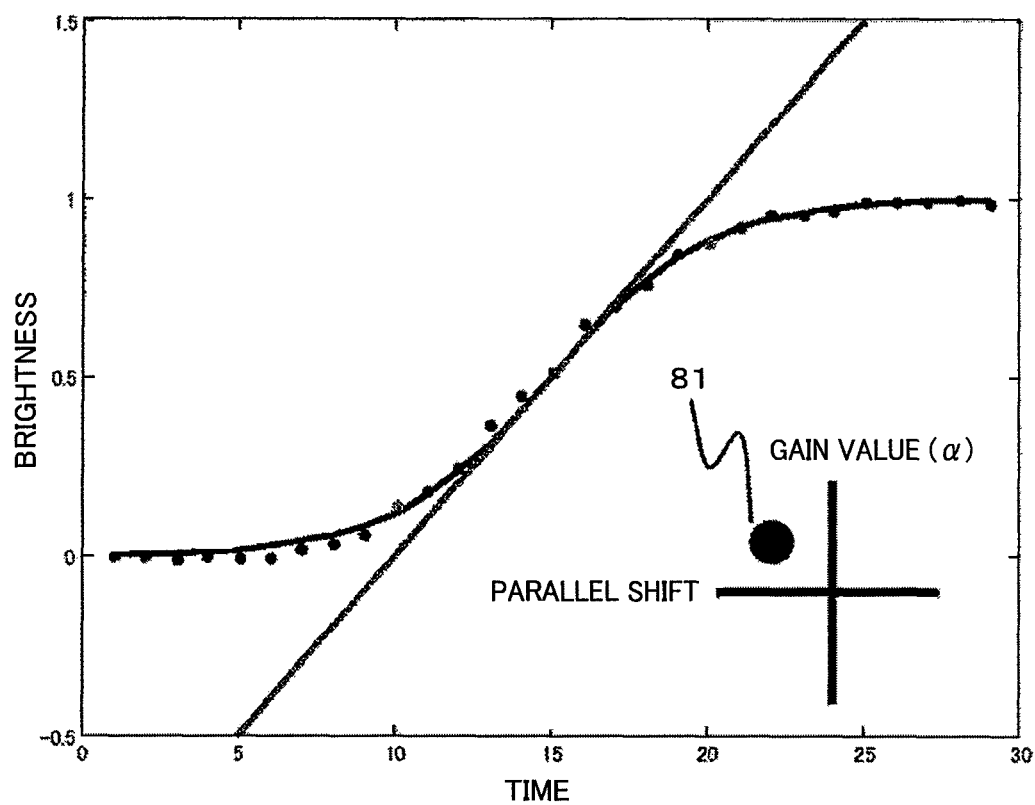
FIG. 8 is a fourth diagram for showing fine-tuning of the model function of the device of the first example.

Further, as shown in FIG. 6, the gain value (α) can be changed by changing a value 61 displayed on the display unit 19, or by sliding a marker 71 on a straight line displayed on the display unit 19 as shown in FIG. 7. Alternatively, as shown in FIG. 8, the gain value (α) can be changed by moving a marker 81 on a two-dimensional space formed using vertical and horizontal lines corresponding to the gain value and the amount of parallel shift, respectively. The result of the fine-tuning is reflected on the function displayed on the display unit 19, and values (ta, tb) to be newly calculated are output.

In the image diagnostic device of the example, the calculated inclination of the tangent line reflects the velocity of the bloodstream, the ta reflects time immediately before the inflow of the administered medical agent such as a contrast medium, and the tb reflects the end time of the inflow. Thus, the range from t=ta to t=tb is fixed as the artery phase.

Figure 9:
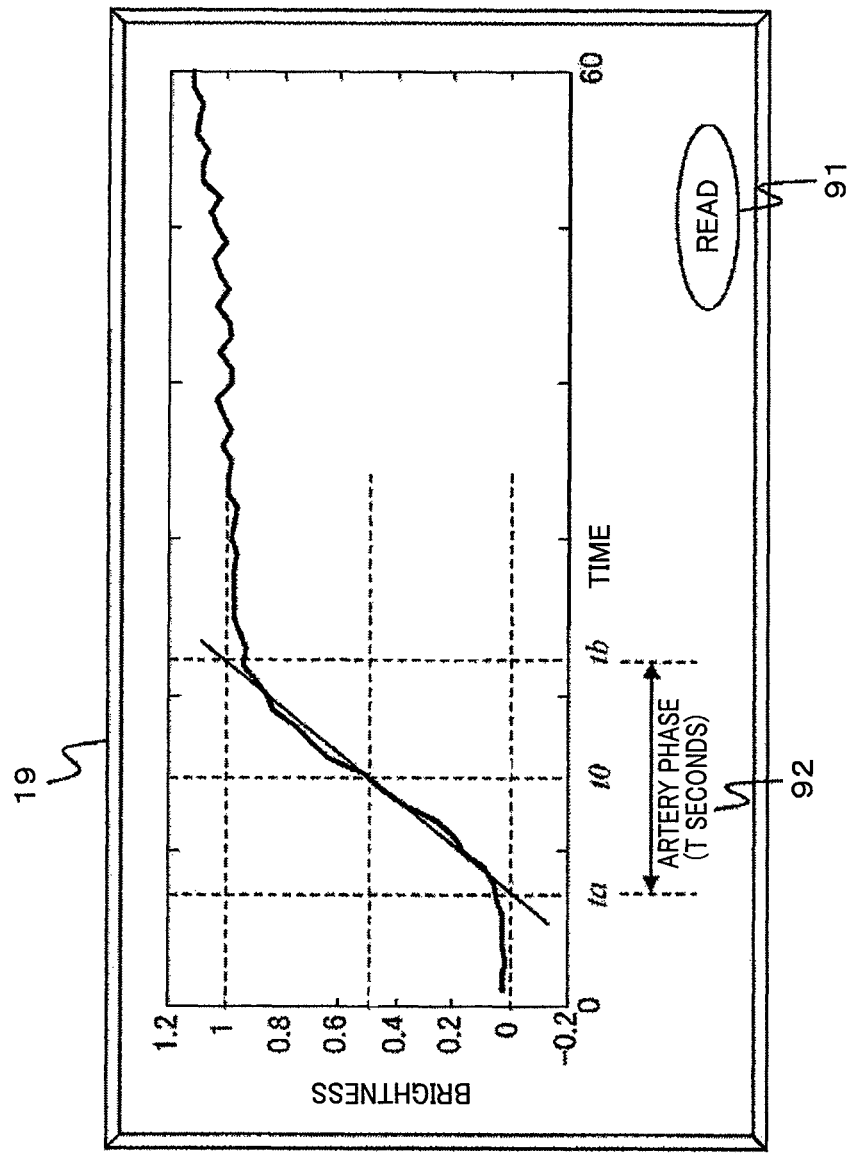
FIG. 9 is a diagram for showing a second example of a display of the device of the first example.
Figure 10:
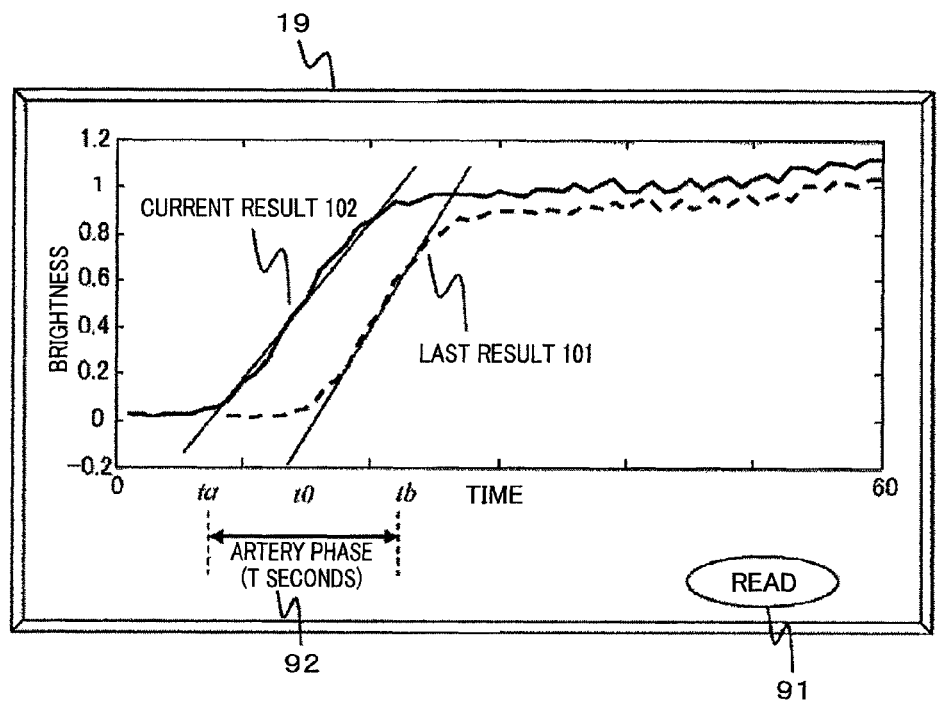
FIG. 10 is a diagram for showing a third example of a display of the device of the first example.

FIG. 9 shows an example of a display configuration showing the artery phase in the image diagnostic device of the example. The ta and tb are displayed on the temporal axis of the time intensity course, and the artery phase 92 can be objectively and visually confirmed. Further, the duration of the artery phase is displayed using a number. Further, selection of a read button 91 displayed on the display unit 19 using the external input unit 20 accesses the memory 18, and a last result 101 that is data acquired in the past is displayed on the display unit 19 while being overlapped with a current result 102 as shown in FIG. 10, so that the time of the inflection point, the inclination of the tangent line, and the values of the ta, tb, and tb–ta can be compared with each other. Further, the image acquisition unit 22 is set as a read access point, so that the image information stored in the image acquisition unit 22 can be input into the image processing unit 21 and can be displayed on the display unit 19 while being overlapped with the processing results.

The above-described first example assumes the image diagnostic device that assesses the artery phase on the basis of the start and end times of the inflow of the contrast medium. However, in the case where the target of interest is a liver, information of a portal phase is contained in the time intensity course in some cases, and the time intensity course and a result of the temporal differentiation at this time are formed as shown in FIG. 11.

Figure 11:
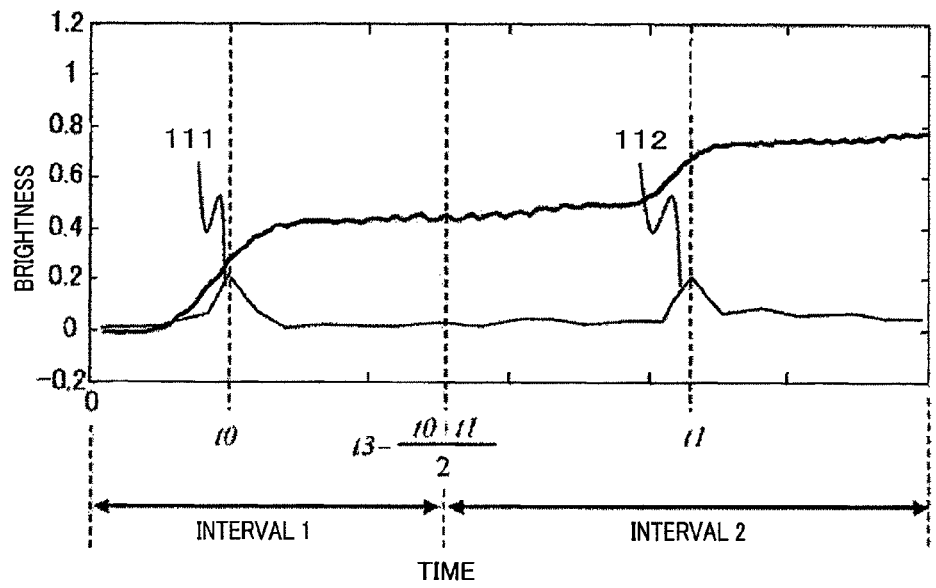
FIG. 11 is a diagram for showing a case of adapting to a portal phase in the device of the first example.

In FIG. 11, two characteristic local maximum values 111, 112 appear in the result of the temporal differentiation process. If the times when the values can be obtained are assumed as t=t0 and t=t1, the t0 corresponds to the center of the artery phase, and the t1 corresponds to the center of the portal phase. Thus, while t3=(t0+t1)/2 is assumed as a boundary, an interval from t=t0 to t=t3 is set as an interval 1 to assess the artery phase, and an interval from t=t3 to t=t2 is set as an interval 2 to assess the portal phase. The processes of the flowchart shown in FIG. 2 are performed at each interval, so that the start and end times of the artery phase and the portal phase are assessed. As a method of assessing the two local maximum values 111112, the maximum value of any one of the local maximum values 111112 is calculated first. Next, the maximum value in a range except a range of about two seconds before and after the maximum value is calculated. The value of two seconds is set because each of the artery phase and the portal phase has approximately one to three seconds, and is appropriately changed depending on a target to be handled.

The example has been described above while assuming a case in which the artery phase is discriminated from the portal phase. However, the same method can be applied to contrast phases of three steps or more. Further, the example has been described above while assuming a case in which the contrast medium is introduced one time. However, the example can be applied to a case in which the contrast medium flows through multiple stages. In the case where the contrast medium flows through multiple stages, the function evaluation unit may perform the above-described approximate process using a function obtained by linearly combining plural S-shaped functions to be obtained to create the model function. Accordingly, the model function with a higher degree of accuracy can be obtained.

The intermediate time (t0) of the artery phase can be calculated by the function evaluation unit 14 of the image diagnostic device in FIG. 1 using the frequency distribution of a time intensity course 121 (f(t)). As shown in FIG. 12, there are two high frequency areas 123 and 124 on the low brightness side and the high brightness side in frequency distribution 122 of the time intensity course 121 (f(t)). The brightness on the low brightness side is assumed as I1, the brightness on the high brightness side is assumed as I2, and the intermediate brightness is assumed as I3=((I1+I2)/2). The intermediate time t0 of the artery phase is obtained from the intersection point of I3 and the time intensity course (f(t)). It should be noted that each of the I1 and I2 may be manually set using the frequency distribution 122. Alternatively, each of the I1 and I2 may be automatically calculated as brightness having a frequency exceeding a value calculated as the average value or the median value of the frequency distribution 122. Further, the to and tb representing the range of the artery phase can be calculated from the intersection points of the I1 and I2 and the time intensity course. In this case, the process of the bloodstream evaluation unit 15 can be omitted because the to and tb are fixed.

It should be noted that the example has been described using an example in which the brightness evaluation unit 13 performs the space average process for the image data in the designated range. However, when the time intensity course is evaluated, a time average process may be performed for the image data in the designated range. For example, the time average process can be performed for image date of 15 frames per second by calculating the time average of adjacent 3 frames so as to set 5 pieces of data in the temporal axis.

According to the above-described first example, it is possible to accurately recognize the start and end of the inflow of the contrast medium into an area where an artery and a portal vein exist by creating the model function that especially match the inclination part of the time intensity course, and it is possible to improve the assessment accuracy of the artery phase or the portal phase.

SECOND EXAMPLE

A device of a second example relates to an example of extracting characteristic information representing a bloodstream dynamic state from information acquired from the image acquisition unit using a result evaluated by the image diagnostic device.

Figure 13:
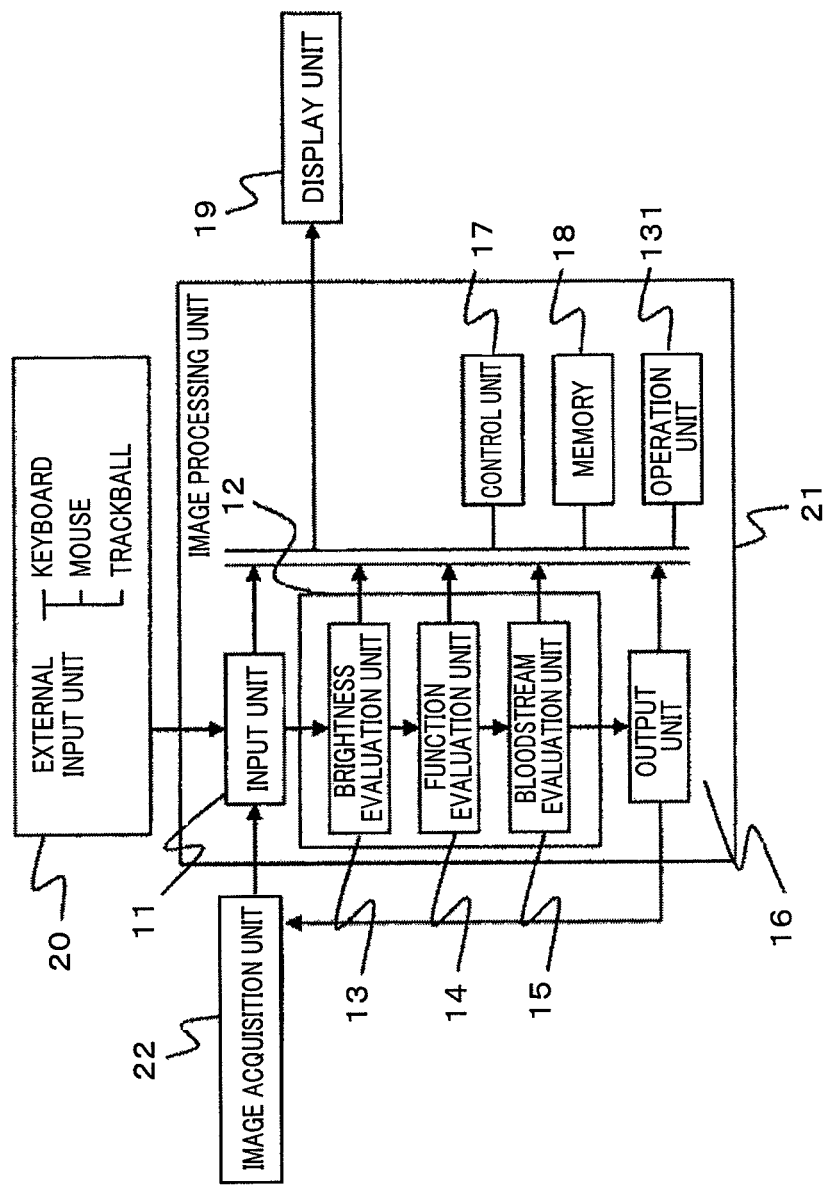
FIG. 13 is a block diagram for showing a configuration example of an image diagnostic device according to a second example.

FIG. 13 shows a functional block diagram of an image diagnostic device according to the second example. The image diagnostic device of the second example is a device in which the image processing unit 21 of the image diagnostic device of the first example is further provided with an operation unit 131 for operating the averaging or the maximum brightness of image information. It should be noted that the operation unit 131 can be realized by executing a program by a CPU that is a processing unit in FIG. 1 of the first example. Even in the example, the steps of assessing the bloodstream dynamic state such as the artery phase or the portal phase on the basis of the information from the image acquisition unit 22 are the same as those of the first example, and thus the explanation thereof is omitted. Further, the example will be described on the assumption that the information input from the image acquisition unit 22 into the input unit 11 is time-series image information and the target of interest is the artery phase.

First, the image information from the image acquisition unit 22 is stored into the memory 18 through the input unit 11. Next, in accordance with the flowchart shown in FIG. 2, the start time ta, the end time tb, and the intermediate time t0 of the artery phase are calculated through the brightness evaluation unit 13, the function evaluation unit 14, and the bloodstream evaluation unit 15 configuring the assessment unit 12. The calculated results are transmitted to the memory 18 through the output unit 16, and the pieces of image information from the image acquisition unit 22 that correspond to t=ta, t=tb, and t=t0 and that are stored in the memory 18 are selected, so that an image of tissue in a living body is displayed on the display unit 19.

Figure 14:
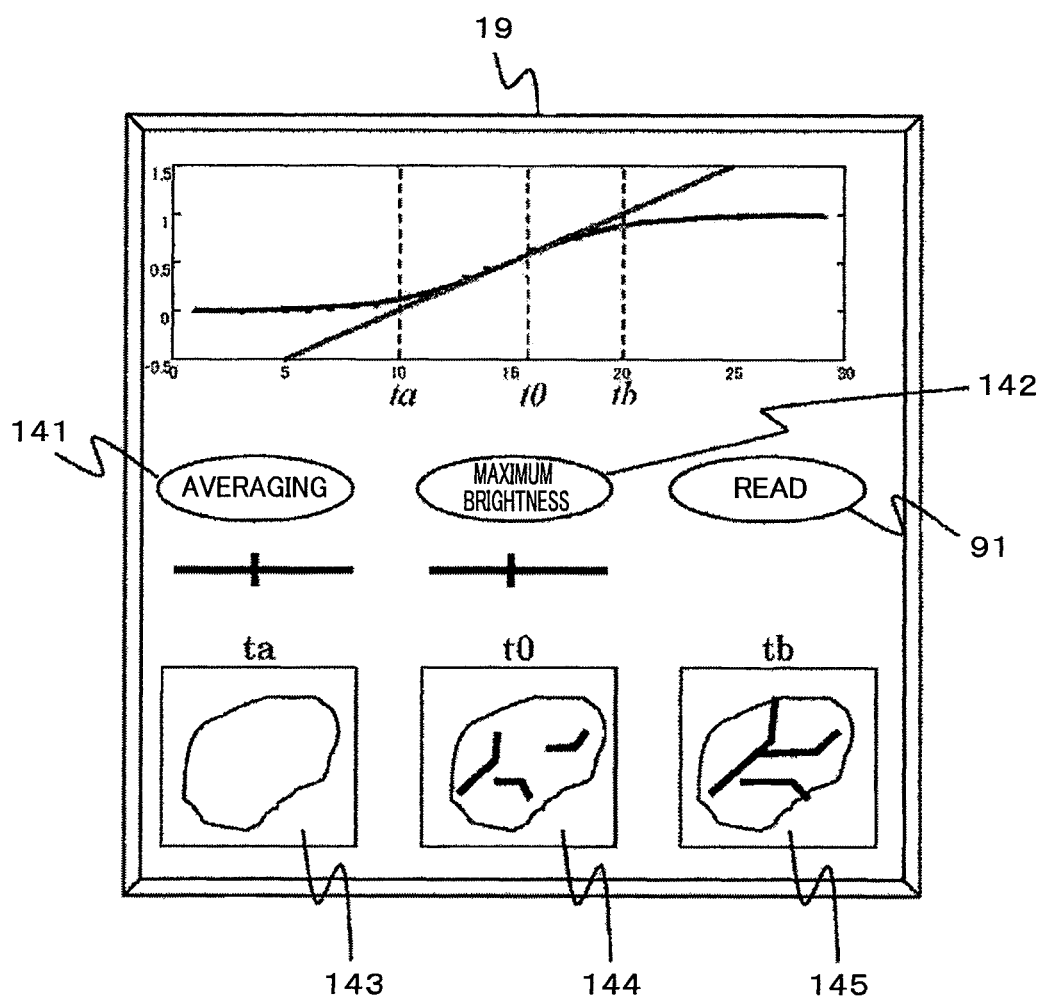
FIG. 14 is a diagram for showing a first example of a display of the device of the second example.

FIG. 14 shows an example of a display configuration of the example. On the display unit 19, displayed are the time intensity course, the model function, the tangent line, and the ta, tb and t0 as similar to FIG. 4. Further, images 143, 144, and 145 corresponding to the ta, tb and t0 are displayed. In terms of time, these images are discretely acquired, and thus the images associated with ta=fix[ta], t0=ceil[t0], and tb=ceil[tb] are selected. In this case, fix[–] is an integral number nearest to the 0 direction, and ceil[–] is an integral number nearest to the positive direction.

In addition to the read button 91, an averaging button 141 and a maximum brightness button 142 are provided on the display unit 19 of the example. When the averaging button 141 is selected using the external input unit 20, the averaged image of each displayed image is calculated by the operation unit 131 to be displayed on the display unit 19. The duration of the averaging is preliminarily set in the image processing unit 21, and can be changed by sliding a marker displayed under the averaging button 141. The result of the change is immediately reflected on the image on the display unit 19. As similar to the above, when the maximum brightness button 142 is selected, a maximum brightness image is displayed. The maximum brightness image is an image configured in such a manner that the brightness of the time-series image data is compared for each pixel and the maximum brightness is selected. The duration for configuring the maximum brightness image can be changed by sliding a marker displayed under the maximum brightness button 141. The function of the read button 19 is the same as that in the first example. By selecting the read button 19, the image information in the past can be selected from the memory 18 or the image acquisition unit 22.

Figure 15:
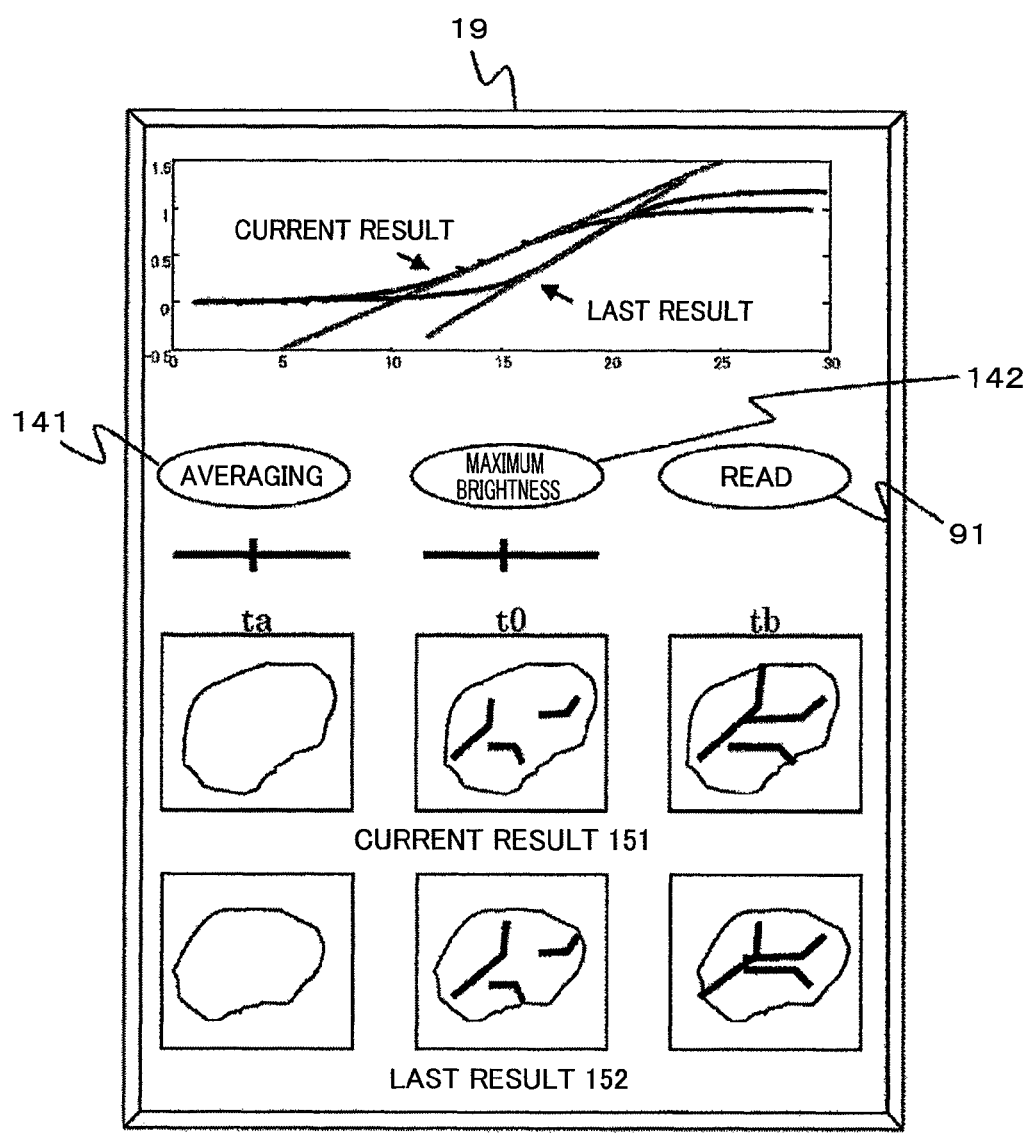
FIG. 15 is a diagram for showing a second example of a display of the device of the second example.

As a display configuration shown in FIG. 15, the selected time intensity course and images are displayed on the display unit 19. The images of current results 151 and last results 152 are arranged and displayed, and the both can be compared to each other. The averaging button 142 and the maximum brightness button 143 function for the image information of the newly-read last results 152.

The main purpose of the second example is to assess the artery phase and the portal phase to present an image at a characteristic time on the basis of the result. Thus, the types of operations performed for the image information in the operation unit 131 are not limited to the averaging and maximum brightness, but can be freely set by the operator.

It should be noted that the present invention is not limited to the above-described examples, but various modified examples may be included. For example, the above-described examples have been described in detail to understandably explain the present invention, and are not necessarily limited to those having the all configurations described above. Further, apart of the configuration in one example can be replaced by a configuration of another example, and the configuration in one example can be added to another example. In addition, a part of the configuration in each example can be added to or replaced by another, or deleted.

Further, a part or all of the configurations, functions, processing units, processing means, and the like may be realized using hardware such as designing with an integrated circuit.

Further, the fact that the configurations, functions, and the like can be realized using software by executing programs realizing the respective functions has been explained. However, information of programs, tables, files and the like for realizing the functions can be stored into not only the memory, but also a recording device such as a hard disk or an SSD (Solid State Drive), or a recording medium such as an IC card, an SD card, or a DVD. Alternatively, the information can be downloaded or installed via a network or the like as needed basis.

REFERENCE SIGNS LIST 11 input unit
12 assessment unit
13 brightness evaluation unit
14 function evaluation unit
15 bloodstream evaluation unit
16 output unit
17 control unit
18 memory
19 display unit
20 external input unit
21 image processing unit
22 image acquisition unit
31, 33, 121 time intensity course
32 temporal differentiation
34 model function
35 tangent line
42 fine-tuning button
51 arrow
61 gain value
71, 81 marker
91 read button
92 artery phase
111, 112 local maximum value
122 frequency distribution
123, 124 high frequency area
131 operation unit
141 averaging button
142 maximum brightness button
143, 144, 145 image

The invention claimed is:

1. An image diagnostic device that evaluates a bloodstream dynamic state of a subject, the device comprising:
an image acquisition unit configured to acquire an image on a basis of a signal received from a subject;
an assessment unit configured to:
approximate a shape of a time intensity course with an S-shaped function to create a model function, and
automatically assess a start and end of an inflow of a contrast medium on a basis of the shape of the time intensity course representing time changes of a brightness of the image, wherein the assessment of the start and end of the inflow of the contrast medium is further based on an inflection point of the model function; and
a display unit configured to display a result assessed by the assessment unit.

2. The image diagnostic device of claim 1, wherein the assessment unit is further configured to perform a fitting process such as a least-square method that is generally used as an approximate process for the time intensity course using the S-shaped function.

3. The image diagnostic device of claim 1, wherein the assessment unit is further configured to calculate a time near an inflection point using a maximum value of a function in which a temporal differentiation process is performed for the time intensity course in an approximate process.

4. The image diagnostic device of claim 1, wherein the assessment unit is further configured to calculate a time near an inflection point using a frequency distribution of the time intensity course in an approximate process.

5. The image diagnostic device of claim 1, further comprising an external input unit configured to input a time near an inflection point of the time intensity course for the time intensity course displayed on the display unit in an approximate process.

6. The image diagnostic device of claim 1, wherein the assessment unit is further on configured to assess the start and end times of the inflow of the contrast medium on a basis of intersection points of a tangent line at an inflection point of the model function and asymptotic lines provided above and under the model function, or on a basis of a frequency distribution of the time intensity course.

7. The image diagnostic device of claim 1, further comprising an external input unit, wherein the display unit is further configured to display the model function, the inflection point of the model function, and the inclination of the tangent line, and wherein the external input unit can finely tune the inflection point and the tangent line of the model function displayed on the display unit.

8. The image diagnostic device of claim 1, wherein in a case where the contrast medium flows in through multiple stages, the assessment unit is further configured to create the model function using a function obtained by linearly combining the plural S-shaped functions to be obtained.

9. The image diagnostic device of claim 1, wherein the display unit is further configured to display the time intensity course representing the time changes, the model function created by the assessment unit, the image information from the image acquisition unit, and the start and end times of the inflow of the contrast medium assessed by the assessment unit.

10. The image diagnostic device of claim 1, wherein the assessment unit is further configured to create the time intensity course after space and time average processes are performed for the image from the image acquisition unit.

11. The image diagnostic device of claim 1, the display unit is further configured to display the image information acquired from the image acquisition unit at the start and end times of the inflow of the contrast medium assessed by the assessment unit.

12. The image diagnostic device of claim 1, further comprising an operation unit configured to operate an averaging or maximizing brightness of the image information acquired from the image acquisition unit.

13. An image assessment method to evaluate a bloodstream dynamic state of a subject, comprising:
acquiring, by an image acquisition unit, an image on a basis of a signal received from a subject;
approximating, by an assessment unit, a shape of a time intensity course with an S-shaped function to create a model function;
automatically assessing, by the assessment unit, a start time and end time of an inflow of a contrast medium on a basis of a shape of a time intensity course representing time changes of a brightness of the image, wherein the assessment, by the assessment unit, of the start and end of the inflow of the contrast medium is further based on an inflection point of the model function; and displaying, by a display unit, a result assessed by the assessment unit.

* * * * *